US010099226B2

(12) United States Patent
Hilgenberg

(10) Patent No.: US 10,099,226 B2
(45) Date of Patent: Oct. 16, 2018

(54) IONIZATION DEVICE

(71) Applicant: Hilgenberg GmbH, Malsfeld (DE)

(72) Inventor: Ingo Hilgenberg, Malsfeld (DE)

(73) Assignee: Hilgenberg GmbH, Malsfeld (DE)

( * ) Notice: Subject to any disclaimer, the term of this patent is extended or adjusted under 35 U.S.C. 154(b) by 216 days.

(21) Appl. No.: 15/200,100

(22) Filed: Jul. 1, 2016

(65) Prior Publication Data
US 2017/0021364 A1 Jan. 26, 2017

(30) Foreign Application Priority Data

Jul. 20, 2015 (EP) .................... 15177563

(51) Int. Cl.
| | | |
|---|---|---|
| *B03C 3/60* | (2006.01) | |
| *B03C 3/12* | (2006.01) | |
| *H01T 23/00* | (2006.01) | |
| *A61L 9/22* | (2006.01) | |
| *B60H 3/00* | (2006.01) | |
| *F24F 3/16* | (2006.01) | |

(52) U.S. Cl.
CPC ................. *B03C 3/60* (2013.01);
*A61L 9/22* (2013.01); *B03C 3/12* (2013.01);
*B60H 3/0071* (2013.01); *F24F 3/166*
(2013.01); *H01T 23/00* (2013.01); *F24F 2003/1682* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 1,839,876 | A | * | 1/1932 | Hartman | A61L 9/015 422/186.18 |
| 3,889,157 | A | * | 6/1975 | Von Berckheim | A61L 9/22 361/230 |
| 4,693,870 | A | * | 9/1987 | Gloor | C01B 13/11 422/186.07 |
| 6,322,759 | B1 | * | 11/2001 | Riege | C01B 13/11 422/186.07 |
| 6,455,014 | B1 | * | 9/2002 | Hammerstrom | A61L 2/14 422/186.04 |
| 6,652,715 | B2 | * | 11/2003 | McLaine | B01J 19/088 204/164 |
| 6,924,495 | B1 | * | 8/2005 | Brickley | A61L 2/10 250/453.11 |
| 7,031,134 | B2 | * | 4/2006 | Izumi | A61L 2/14 361/231 |
| 7,037,468 | B2 | * | 5/2006 | Hammerstrom | A61L 2/14 204/164 |

(Continued)

FOREIGN PATENT DOCUMENTS

DE 10254135 * 6/2004
EP 1 348 448 A1 10/2003
(Continued)

*Primary Examiner* — Robert A Hopkins
*Assistant Examiner* — Sonji Turner
(74) *Attorney, Agent, or Firm* — Seyfarth Shaw LLP

(57) ABSTRACT

The present invention relates to a glass parts release prevention, or specifically a glass splinter protection, for ionization devices, wherein a glass bulb is at least partially covered by a polymer film. The electrode is arranged within the glass bulb, and an outer electrode is slid over the outer contours of the polymer film.

23 Claims, 3 Drawing Sheets

(56) References Cited

U.S. PATENT DOCUMENTS

| | | | | |
|---|---|---|---|---|
| 7,120,006 | B2* | 10/2006 | Sekoguchi | A61L 9/22 361/230 |
| 7,312,973 | B2* | 12/2007 | Sekoguchi | A61L 9/22 361/231 |
| 7,449,053 | B2* | 11/2008 | Hallam | A61L 9/015 96/52 |
| 7,799,290 | B2* | 9/2010 | Hammerstrom | A61L 2/14 422/121 |
| 7,839,068 | B2* | 11/2010 | Hayashi | A01M 1/2083 313/489 |
| 8,092,643 | B2* | 1/2012 | Kurunczi | A61L 2/14 156/345.43 |
| 8,604,694 | B2* | 12/2013 | Yeulash | H05H 1/2406 315/32 |
| 8,696,996 | B2* | 4/2014 | Albrecht | A61L 9/22 422/186.04 |
| 8,747,754 | B2* | 6/2014 | Abate | B03C 3/383 29/592.1 |
| 8,773,838 | B2* | 7/2014 | Takeda | A61L 9/22 361/230 |
| 9,114,356 | B2* | 8/2015 | Gurman | B01D 53/32 |
| 9,597,424 | B2* | 3/2017 | Gurman | B01D 53/32 |
| 9,616,144 | B2* | 4/2017 | Shannon | A61L 2/202 |
| 9,757,487 | B2* | 9/2017 | Roy | A61L 2/14 |
| 2005/0031503 | A1* | 2/2005 | Fox | A61L 9/22 422/186.04 |
| 2007/0166209 | A1* | 7/2007 | Zimmerman | A61L 2/202 422/186.07 |
| 2009/0135538 | A1 | 5/2009 | Yasuoka et al. | |
| 2010/0071397 | A1* | 3/2010 | Takeda | A61L 9/22 62/264 |
| 2012/0154973 | A1* | 6/2012 | Vaynerman | B03C 3/383 361/231 |
| 2015/0340207 | A1* | 11/2015 | Holbeche | A61B 18/042 156/345.33 |
| 2015/0351212 | A1* | 12/2015 | Deane | A61L 9/16 313/231.31 |

FOREIGN PATENT DOCUMENTS

| | | |
|---|---|---|
| WO | 2002089569 A1 | 11/2002 |
| WO | 2004076052 A2 | 9/2004 |
| WO | 2010014635 A1 | 2/2010 |
| WO | WO2011002006 * | 6/2011 |

* cited by examiner

IONIZATION DEVICE

The present application relates to ionization devices.

TECHNICAL FIELD OF THE INVENTION

Ionization devices are used for the production of ionized air, being used in various fields, for example in air-conditioning systems of public buildings and vehicles, air-conditioning technology and in air treatment in chemically and biologically contaminated areas. Further applications are defense technology, building technology and motor vehicles.

The ions contained in the ionized air can attach to bacteria and viruses, thereby destroying them. Furthermore, those ions can bind odors, dust and other micro-particles from the air.

BACKGROUND OF THE INVENTION

Ionization devices generally comprise two electrodes and a glass part, e.g. a glass bulb, separating both electrodes.

On both electrodes, a high voltage of between 2000-3000 V can be applied in order to establish an electric field between both electrodes, which causes the air around the ionization device to generate and release ions.

WO 2010/014635 A1 shows an example of an ionization device, here configured as a bi-polar ionization device comprising a glass tube and a tube socket for an air-treatment apparatus. Here, the electrodes are formed as net electrodes, each of them arranged at the outer side and the inner side of the glass tube respectively, wherein the electrical connector is provided to electrically connect the inner electrode to a high voltage.

However, ionization devices comprise glass parts, which could break particularly under the influence of large voltages, with the potential problem that glass splinters can be generated and released. Therefore, the scope of the use of conventional ionization devices is constrained or even strictly limited, and especially in any area related to food or food processing (e.g. fishery, meet processing factories, dairy industry), concerns are raised and consequently other decontamination techniques are favoured.

It is therefore still a need and thus an object of the present invention to provide an ionization device with improved properties or favourable use attributes.

SUMMARY OF THE INVENTION

A main aspect of the invention resides in providing an ionization device with a polymer film, preferably in the form of a heat-shrinkable polymer tubing, on at least a part, but preferable all over the outer circumference of the glass part of the ionization device.

Such provision of polymer film ensures that the ionization device's glass bulb and beneficially the whole outer surface thereof can be covered by a suitable polymer film to prevent any potentially broken glass parts being releasable from the device. In particular a heat-shrinkable polymer tubing has a generally homogeneous structure and homogeneous thickness in axial and radial extension, as it is pre-manufactured and linearly and evenly shrinks to be adapted in close-fitting manner to the glass bulb regarding its diameter.

A polymer film can perfectly match with the glass part of the device and thereby prevent even small glass parts or splinters to escape after breakage. These beneficial properties and use attributes allow to make now use of ionization devices even in the food sector.

The provision of a polymer film on a glass bulb for an ionization device has turned out to lead to a device with improved properties, as glass splintering could be reduced or even suppressed.

However, specific solvent-based processes of applying a polymer film onto a glass bulb, like spray coating with solvent-containing polymers based on PE, PU and PP, may lead to less preferable polymer film protection and thus may optionally be omitted, for example, for some layers obtained by such processes, to have satisfactory broken glass protection, a high layer thickness was required and/or the layers were not smooth enough; further, a sticky surface may be obtained by such processes in some cases, leading to difficulties in the assembly of the ionization device; also a coating of the glass bulb with paints or varnishes may lead to inhomogeneous thicknesses in some cases, such as with PU-based varnish; and moreover, ions and ozone generated by the ionization device could lead to aging of a PU-based varnish, thereby leading to fragility of the surface and to discoloration.

The use of a heat-shrinkable polymer tubing is particularly preferred, as it resulted in a smooth film with a generally homogeneous thickness. Suitable materials for a polymer film, in particular since these have the property of being shrunk upon heating, are in general fluorine-containing polymers such as polytetraflouroethylene (PTFE), polyvinylidene fluoride (PVDF), polyvinylidenefluoride (PVDF), crosslinked fluoropolymers (e.g. FPMX), polyvinylchloride (PVC), polyesters such as polyethylene terephthalate (PET), ethylene-based polymers such as polyethylene (PE) (which can also be modified by e.g. radiation-crosslinking), further polyolefins (e.g. PO-X, POF), ethylene-vinyl acetate copolymer (EVA), elastomers (e.g. radiation-crosslinked elastomers), silikone, etc.

The heat-shrinkable polymer tubing material can be monoaxially or biaxially stretched. Also possible are multi-layered polymer films composed of a multitude heat-shrinkable polymer tubings respective made of the same or different polymers using one or more aforementioned polymers.

In order to cope with special further needs for ionization devices, the polymer material for forming the polymer film is most preferably chosen by having sufficient tear resistance, having the capacity of being folded and compressed over the glass bulb at its end, and having sufficient adhesion power on glass after heat shrinking. Further, a destruction of the polymer film, e.g. by scratching, should be avoided. Further, the polymer material for a polymer film most preferably has a sufficient resistance against decomposition by high voltages, ionized air and ozone. Further, the material should be resistant against cutting, e.g. by glass splinters.

The provision and use of a polymer film, in particular a heat-shrinkable polymer tubing, on the basis of a fluorine-containing polymer, in particular polytetraflouroethylene (PTFE), has been demonstrated to provide an excellent balance of properties in order to meet the particular needs for ionization devices in a best manner.

Firstly, the surface of fluorine-containing polymers such as PTFE is very smooth and even, dust cannot adhere to it. Furthermore, especially PTFE is very tear-proof and is extremely stable even in thin layers. Moreover, especially PTFE can be densely pushed together and compressed at the end of the bulb via heating. PTFE hardly influences the ionization effect, as it can be made into film in a very thin layer, especially if a heat-shrinkable polymer tubing made of this material is used. Further, fluorine-containing polymers and especially PTFE is insensitive towards ozone and ionization, and is further stable against aging due to environmental effects. Furthermore, fluorine-containing polymers such as PTFE allow that the outer electrode can be slid very easily onto the outer surface of the bulb covered with a corresponding polymer film, in particular when applied in the form of a heat-shrinkable polymer tubing. As stated above, the surface is very smooth and does not cause any friction. This has remarkable advantages during the assembly of the ionization bulb.

The electrodes may mainly comprise aluminum, stainless steel, silver, chromium, gold or copper and are preferably made of a mesh-like or net-like material. This mesh-like or net-like material could be wire-mesh or stretch-grit. Also materials with a core-shell structure, comprising more than one metal, can be used. A connector can seal an open end of the glass bulb, on the other hand can connect the inner electrode with any electric power source. For being used with a connector, it is possible that a certain outer part of the glass bulb remains uncovered, which shall be covered by inner contours of the connector, and preferably a sealing of the connector may form an effective sealing with the glass bulb.

In the following, preferred, but non-limiting embodiments of the invention are described in detail by reference to the enclosed drawings.

DETAILED DESCRIPTION OF THE EMBODIMENTS

Figure 1:
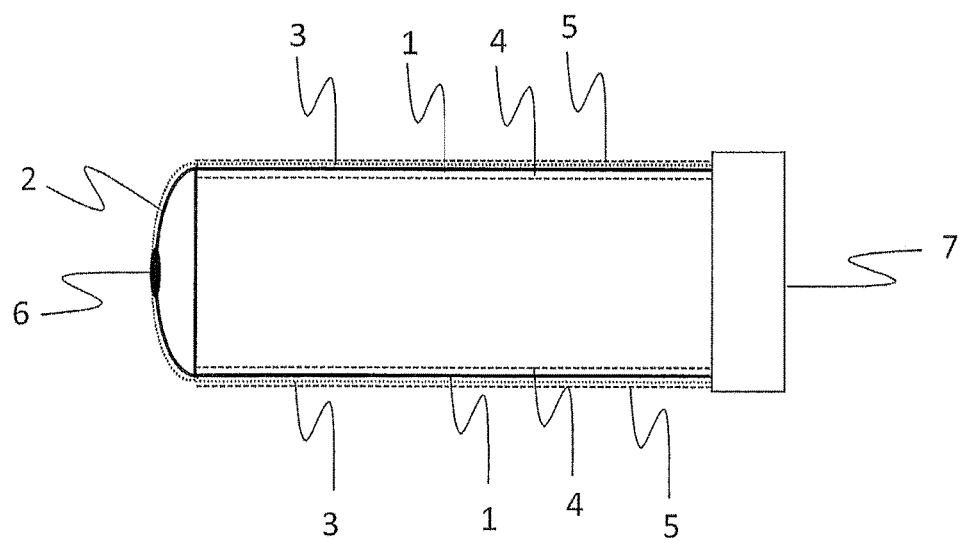
FIG. 1 is an isometric view of an ionization device according to a first embodiment of the present invention.

FIG. 1 shows an embodiment of the ionization device comprising a glass bulb, here in a preferred form of a glass tube, which is closed on the one side with a bottom 2, being integrally formed with the glass tube 1. The glass tube 1 and the bottom 2 are covered, in the present preferred embodiment fully covered, by a layer of polymer film 3. In a further preferred form of the embodiment, the polymer film 3 is applied in the form of a heat-shrinkable tubing. The polymer film 3 is thus preferably formed by a heat-shrinkable polymer tubing. The one end section of the heat-shrinkable polymer tubing is folded and compressed to form a compressed part 6. The inner electrode 4, formed as a net electrode, is inserted into the glass tube. On the outer side, the outer electrode 5 is provided directly onto the polymer film 3, tightly fitting on the glass tube 1 including the bottom 2. The whole glass tube is closed at its open end by a connector 7, also providing the possibility of providing electric connection with the inner net electrode 4.

Figure 2:
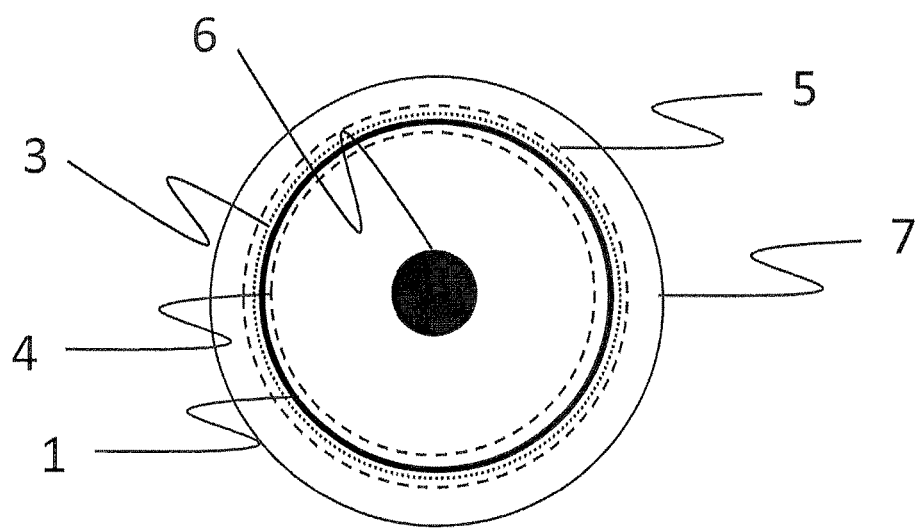
FIG. 2 is a section view of the ionization device of FIG. 1.

FIG. 2 shows a section view of the ionization device. Herein, especially a compressed part 6 becomes visible, where a part of the polymer film 3 is compressed to form an end at the bottom 2 of the tube.

From FIGS. 1 and 2, it can be recognized that the glass bulb 1 effectively separates the inner electrode 4 and the outer electrode 5. In the present preferred embodiment, the glass bulb 1 is fully covered by the (preferably heat-shrinkable) polymer film 3, which tightly fits on the outer contours of the glass bulb 1 including its bottom 2. It can also be seen that the outer electrode 5 closely fits onto the outer circumference of the polymer film 3. On the end part of the glass bulb 1, i.e. on the outermost position of the bottom 2, the polymer film 3 is compressed and cut, forming an compressed part 6. Thus, the whole glass bulb 1 is effectively covered by shrunk polymer, so that no splinters can be released even if the glass bulb breaks.

A production of an ionization device as described above can easily be implemented and further be applied to any conventional type or arrangement of ionization devices.

In the following, a preferred embodiment of the production of a ionization device with a polymer film 3 is described, using a heat-shrinkable polymer tubing.

At first, a glass bulb 1 comprising a bottom 2 is provided.

Subsequently, a heat-shrinkable polymer tubing is provided to form a polymer film on the outer side of the glass bulb 1 including the bottom 2, wherein the inner diameter of the heat-shrinkable polymer tubing 3 can be generally the same or larger than the outer diameter of the glass bulb 1.

In the subsequent step, the glass bulb 1 including the bottom 2 and the heat-shrinkable polymer tubing 3 are heated, until the heat-shrinkable polymer tubing 3 after being shrunk closely fits on the outer surface of the outer diameter of the glass bulb 1 including the bottom 2, thereby forming a polymer film 3. This heating is preferably preformed in an oven or a heat tunnel (possibly equipped with a conveyor), but could also be performed with a heat gun. In the area of the bottom 2, the polymer film 3 is cut at some point and pressed together to form a compressed part 6 in order to have a complete sealing of the bottom 2 by the polymer film 3.

Subsequently, the inner electrode is inserted into the glass bulb, and the outer electrode is slid over the outer diameter of the polymer film 3 in order to be fixed there.

The heating step can be performed at a temperature ramp up to a temperature suitable to shrink the shrinkable polymer, for example a range of 80° C. to 360° C., preferably from 320° C. to 340° C.

When the desired final heating temperature is reached, this temperature is preferably kept for 10 sec to 1 h, even more preferably 5 min to 15 min in order to obtain a full shrinking of the heat-shrinkable polymer tubing 3 and to achieve that the heat-shrinkable polymer tubing 3 closely fits on the outer diameter of the glass bulb 1 and the bottom 2. One preferential arrangement during the production of the ionization device is to have the heat-shrinkable polymer tubing 3 firstly overlap the open end of the glass bulb 1 and then folding it over the edge of the open end of the glass bulb 1 before heating, thus a part of the heat-shrinkable polymer tubing 3 projects into the interior of the glass bulb 1. In this case, the shrinking of the heat-shrinkable polymer tubing 3 starts in the interior of the glass bulb 1, proceeds over the glass bulb 1, thereby preventing the formation of air bubbles between the glass bulb 1 and the heat-shrinkable polymer tubing 3. Thereby, it can be achieved that the heat-shrinkable-tubing 3 closely fits on the glass bulb and the bottom 2.

The process according to the present invention has a further advantage that up to tens of bulbs or even some 100 bulbs can be treated simultaneously, and because of the preferred form of the heat-shrinkable polymer tubing 3, the ionization devices can be heated up to a temperature of approximately 340° C. At an appropriate time, the heat source is switched off and the oven including the glass bulbs is cooled down. After, the glass bulbs can be taken out of the oven.

One preferred solution is to cut the shrunk and cooled polymer film at the open end for approximately 1 cm before mounting the connector 7 to the glass bulb 1. Here, an optimal adhesion between glue applied to the connector 7 can be obtained, and simultaneously, the connector 7 still overlaps the part of the glass bulb 1 in which the heat-shrinkable polymer tubing 3 is applied, so that no areas of the glass bulb 1 remain uncovered by the heat-shrinkable polymer tubing 3.

Figure 3:
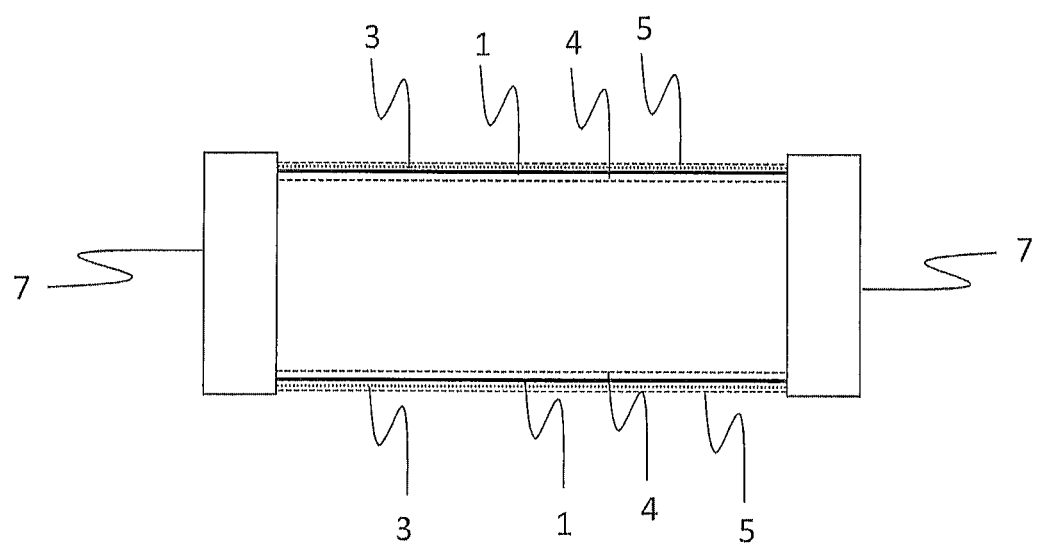
FIG. 3 is an isometric view of an ionization device according to a second embodiment of the present invention.

FIG. 3 shows a second embodiment of the present invention. Herein, the glass bulb 1 does not have any glass bottom. The glass bulb is open on both ends, but sealed with a connector 7 on both ends. The polymer film 3, which preferably is in the form of a heat-shrinkable polymer tubing, the inner electrode 4 and the outer electrode 5 are provided in a same or similar manner as presented in the first embodiment.

In the following, the production of the second embodiment of the ionization device with a heat-shrinkable polymer tubing is described.

At first, a glass bulb 1 is provided. Subsequently, a heat-shrinkable polymer tubing is provided on the outer side of the glass bulb 1, wherein the inner diameter of the polymer film 3 (preferably in the form of a heat-shrinkable polymer tubing) can be generally the same or larger than the outer diameter of the glass bulb 1.

In a subsequent step, the glass bulb 1 and the preferred heat-shrinkable polymer tubing 3 are heated, until the heat-shrinkable polymer tubing 3 after being shrunk closely fits on the outer surface of the outer diameter of the glass bulb 1. This heating is preferably preformed in an oven or a heat tunnel (possibly equipped with a conveyor), but could also be performed with a heat gun.

Subsequently, the inner electrode is inserted into the glass bulb, and the outer electrode is slid over the outer diameter of the polymer film 3 in order to be fixed there. Afterwards, connectors 7 are provided on both open ends of the glass bulb 1.

The present invention is not limited to the embodiments as described above. It is for example possible that the glass bulb 1 has an oval, triangular, quadratic or polygonal cross-section. Also the bottom 2 can have various form. The cross-section of the glass bulb 1 could have different forms or geometries and could even have edges. Further, the polymer film 3 such as a heat-shrinkable polymer tubing can still closely fit on the outer contours of the glass bulb 1 of any such modified forms.

Further, a moulded part using a heat-shrinkable polymer tubing 3 could be used, for example in the shape of a hose including a bottom. Such a moulded part could easily be applied to a glass bulb 1 including a bottom 2 and would closely fit on such a specific glass bulb.

Further, the glass bulb 1 could be fabricated without a bottom 2 at all, and any other suitable sealing means for the glass bulb 1 could be applied. Furthermore, the connector device 7 could be suitably adapted in order to also adhere to the polymer film 3, so the polymer film 3 could even cover section(s) where the connector 7 covers the glass bulb 1.

Other options for applying the polymer film 3 onto the glass bulb 1 are painting and spraying of liquid polymer or dipping the glass bulb into a liquid polymer melt.

Further, it is possible to use a polymer film 3 together with any kind of glue applied to the inner circumferential area of the polymer film 3. This glue can serve as a linking layer between glass bulb 1 and polymer film 3. Such a linking layer is especially suitable for polymer films 3, preferably in the form of heat-shrinkable polymer tubings, made of polyolefins.

The present invention relates to a glass parts release prevention, specifically a glass splinter protection, for ionization devices, wherein a glass bulb 1 is at least partially covered by a polymer film 3. The electrode 4 is arranged within the glass bulb 1, and an outer electrode 5 is slid over the outer contours of the polymer film 3.

The invention claimed is:

1. An ionization device comprising:
   a glass bulb having an inner side and an outer side; and
   a plurality of electrodes including an inner electrode provided within the glass bulb and an outer electrode provided on the outer side of the glass bulb so that the glass bulb is disposed between at least the inner and outer electrodes, thereby isolating the inner and outer electrodes from each other; and
   a polymer film at least partially covering the glass bulb.

2. The ionization device according to claim 1, wherein the polymer film at least partially covering the glass bulb is based on a polymer selected from a group consisting of polytetraflouroethylene (PTFE), polyvinylidene fluoride (PVDF), polyvinylidenefluoride (PVDF), crosslinked fluoropolymer, polyvinylchloride (PVC), polyesters, ethylene-based polymers, further polyolefins, ethylene-vinyl acetate copolymer (EVA), elastomers, and silicone.

3. The ionization device according to claim 1, wherein a polymer forming the polymer film is a shrinkable polymer.

4. The ionization device according to claim 1, wherein the polymer film is a heat-shrinkable polymer tubing.

5. The ionization device according to claim 1, wherein the polymer film is based on a fluorine-containing polymer.

6. The ionization device according to claim 1, wherein the polymer film is based on polytetrafluoroethylene (PTFE).

7. The ionization device according to claim 1, wherein the electrodes include at least one material selected from a group consisting of aluminum, stainless steel, silver, copper, chromium and gold.

8. The ionization device according to claim 1, wherein the electrodes are made of a mesh-like material.

9. The ionization device according to claim 8, wherein the mesh-like material is wire mesh or stretch grid.

10. The ionization device according to claim 1, wherein the glass bulb is tube-shaped.

11. The ionization device according to claim 1, further comprising a glass bottom formed integrally with the glass bulb and closing one end of the glass bulb.

12. The ionization device according to claim 1, wherein the glass bulb includes a glass portion accessible to an outside of the glass bulb, and wherein an entirety of the glass portion is covered by the polymer film.

13. The ionization device according to claim 1, wherein the polymer film extends beyond the outer side of the glass bulb and is folded into the inner side of the glass bulb.

14. A process for the production of an ionization device, the process comprising the steps of:
   providing a glass bulb having an outer circumferential surface;
   providing a polymer film over at least a part of the outer circumferential surface of the glass bulb;
   inserting an inner electrode into the glass bulb; and
   placing an outer electrode above at least a part of the outer circumferential surface of the polymer film.

15. The process for the production of an ionization device according to claim 14, wherein the step of providing a polymer film over at least a part of the outer circumferential surface of the glass bulb comprises providing a heat-shrinkable polymer tubing over at least a part of the outer circumferential surface of the glass bulb, wherein an inner diameter of the heat-shrinkable polymer tubing is equal to or larger than an outer diameter of the glass bulb, and further comprising heating the heat-shrinkable polymer tubing to thereby shrink the heat-shrinkable polymer tubing until the heat-shrinkable polymer tubing closely fits on at least a part of the outer circumferential surface of the glass bulb.

16. The process according to claim 14, wherein an entire accessible outer circumferential surface of the glass bulb is covered by the polymer film.

17. The process according to claim 15, wherein the heating is performed in an oven or a heat tunnel.

18. The process according to claim 15, wherein the heating step is performed up to a temperature of 80° C. to 360° C.

19. The process according to claim 15, wherein the glass bulb is maintained at the final heating temperature for 10 seconds to 1 hour.

20. The process according to claim 15, wherein the heat-shrinkable polymer tubing is folded and pressed at a bottom of the glass bulb.

21. The process according to claim 15, wherein the polymer film is folded over an edge of an open end of the glass bulb before heating, thereby projecting into an interior of the glass bulb.

22. The process according to claim 14, wherein the polymer film is cut a distance of approximately 1 cm from the open end of the glass bulb.

23. A method of using an ionization device, comprising:
providing a glass bulb and electrodes, the electrodes including an inner electrode provided within the glass bulb and an outer electrode provided on an outer circumference of the glass bulb so that the glass bulb is disposed between the inner and outer electrodes, thereby isolating the inner and outer electrodes from each other, and
providing a polymer film at least partially covering the glass bulb to prevent the ionization device from releasing broken glass parts when the glass parts are broken from the ionization device; and
using the ionization device on food.

* * * * *